(12) United States Patent
King

(10) Patent No.: US 6,753,341 B1
(45) Date of Patent: Jun. 22, 2004

(54) INHIBITION OF PKC TO TREAT PERMABILITY FAILURE

(75) Inventor: George Liang King, Dover, MA (US)

(73) Assignee: Joslin Diabetes Cancer, Inc., Boston, MA (US)

( * ) Notice: Subject to any disclaimer, the term of this patent is extended or adjusted under 35 U.S.C. 154(b) by 0 days.

(21) Appl. No.: 09/524,459

(22) Filed: Mar. 10, 2000

Related U.S. Application Data

(60) Provisional application No. 60/124,043, filed on Mar. 12, 1999.

(51) Int. Cl.$^7$ .............................................. A61K 31/40
(52) U.S. Cl. ....................................... 514/414; 514/458
(58) Field of Search .................................. 514/414, 458

(56) References Cited

U.S. PATENT DOCUMENTS

| | | |
|---|---|---|
| 5,736,564 A | 4/1998 | Elliott et al. ................. 514/414 |
| 5,929,106 A | 7/1999 | Elliott et al. ................. 514/414 |

OTHER PUBLICATIONS

Hu et al., "Protein Kinase C activates ATP–sensitive K+ current in human and rabbit ventricular myocytes", Circulation Research, vol. 78, No. 3, pp. 492–498, 1996, see abstract.*

Sitter et al., "High glucose increases prostaglandin E2 synthesis in human peritoneal mesothelial cells: Role of hyperosmolarity.", Journal of the American Society of Nephrology, vol. 9, No. 11, pp. 2005–2012, Nov. 1998.*

Sitter et al., "High glucose increases prostaglandin E2 synthesisi in human peritoneal mesothelial cells: Role of hyperosmolarity.", Journal of the American Society of Nephrology, vol. 9, No. 11, pp. 2005–2012, Nov. 1998.*

\* cited by examiner

*Primary Examiner*—Dwayne C. Jones
(74) *Attorney, Agent, or Firm*—Fish & Richardson P.C.

(57) ABSTRACT

The invention features a method of treating a subject, e.g., a subject having permeability disjunction, which includes administering to the subject peritoneal dialysis fluid which includes an inhibitor of PKC, e.g., an inhibitor of PKC β. The invention also features an improved peritoneal dialysis fluid and methods of making such dialysis fluid.

10 Claims, 4 Drawing Sheets

INHIBITION OF PKC TO TREAT PERMABILITY FAILURE

This application claims the benefit of a previously filed Provisional Application No. 60/124,043, filed Mar. 12, 1999, the contents of which is incorporated in its entirety.

BACKGROUND OF THE INVENTION

The invention relates to peritoneal dialysis fluids, and methods of making and using them. More particularly, it relates to the methods for preventing and treating complications due to peritoneal dialysis.

Peritoneal dialysis can be used to treat patients having chronic renal failure. In this procedure, peritoneal dialysis fluid is introduced into the peritoneal cavity of a subject. The fluid generally has a high glucose level, often in the 100 mM range. Introduction of this relatively high molarity fluid into the peritoneum causes the osmotic extraction of toxins, for example, urea creatinine, and other substances normally removed by the kidney, from the blood. It can also reduce the level of fluid in the patient.

SUMMARY OF THE INVENTION

The invention is based, in part, on the discovery that the use of peritoneal dialysis fluid, especially prolonged use, can result in decreasing permeability between the peritoneal dialysis fluid and the blood compartment, that high levels of glucose are involved in changes in the cells lining the peritoneum, that the high glucose levels activate PKC, and that the inhibition of PKC can prevent this chronic complication. The invention can treat an undesirable decrease in the efficiency of exchange between the peritoneal dialysis fluid and the vascular compartment.

Accordingly, the invention features, a method of treating a subject. The method includes:
 introducing peritoneal dialysis fluid into the peritoneum of the subject; and
 inhibiting a PKC in the subject,
thereby treating said subject.

In a preferred embodiment, an inhibitor of PKC is included in the peritoneal dialysis fluid. The inhibitor is preferably a specific inhibitor of PKC. The inhibitor can be an inhibitor of a PKC J, e.g., J1 or J2, K, L, or other isoform. The inhibitor can be, for example, a bis (indolyl) maleimide, for example, the PKC J inhibitor LY333531, which is described in Ishi et al. (1996) Science 272:728–731, hereby incorporated by reference. LY333531 can be present in the dialysis fluid at about 1–1,000, 5–750, 20–500, but more preferably 50–500 nM.

In a preferred embodiment, the concentration of glucose in the peritoneal dialysis fluid is 200 nM.

Peritoneal dialysis fluid of the invention is particularly useful for subjects who are already peritoneal dialysis patients. In preferred embodiments, the subject has been a peritoneal dialysis patient for at least 2, 4, 6, 12, or 24 months, e.g., the subject has been administered peritoneal dialysis fluid, either one with or without a PKC inhibitor, periodically for at least 2, 4, 6, 12, or 24 months, or it has been at least 2, 4, 6, 12, or 24 months since the subjects first peritoneal dialysis administration. Peritoneal dialysis fluid of the invention can be administered to patients who have already developed permeability disjunction.

In other embodiments peritoneal dialysis fluid of the invention is useful for subjects who have not yet had peritoneal dialysis. Peritoneal dialysis fluid of the invention can be administered to patients who have not yet developed permeability disjunction.

In another aspect, the invention features, a method of treating a subject. The method includes:
 introducing peritoneal dialysis fluid and an inhibitor of a PKC into the subject,
thereby treating the subject.

In a preferred embodiment, the peritoneal dialysis fluid and PKC inhibitor are co-administered to the subject; the peritoneal dialysis fluid and PKC inhibitor are introduced separately into the subject; the peritoneal dialysis fluid and PKC inhibitor are combined prior to introduction into the subject and administered together.

In a preferred embodiment, an inhibitor of PKC is included in the peritoneal dialysis fluid. The inhibitor is preferably a specific inhibitor of PKC. The inhibitor can be an inhibitor of a PKC $\beta$, e.g., $\beta 1$ or $\beta 2$, $\gamma$, $\delta$, or other isoform, or combinations thereof. The inhibitor can be, for example, a bis (indolyl) maleimide, for example, the PKC $\beta$ inhibitor LY333531. LY333531 can be present in the dialysis fluid at about 1–1,000, 5–750, 20–500, but more preferably 50–500 nM.

In a preferred embodiment, the concentration of glucose in the peritoneal dialysis fluid is 200 nM.

In a preferred embodiment, the subject is administered a second, third, fourth, or fifth, infusion of peritoneal dialysis fluid.

Peritoneal dialysis fluid of the invention is particularly useful for subjects who are already peritoneal dialysis patients. In preferred embodiments the subject has been a peritoneal dialysis patient for at least 2, 4, 6, 12, or 24 months, e.g., the subject has been administered peritoneal dialysis fluid, either one with or without a PKC inhibitor, periodically for at least 2, 4, 6, 12, or 24 months, or it has been at least 2, 4, 6, 12, or 24 months since the subjects first peritoneal dialysis administration. Peritoneal dialysis fluid of the invention can be administered to patients which have already developed permeability disjunction.

In other embodiments, peritoneal dialysis fluid of the invention is useful for subjects who have not yet had peritoneal dialysis. Peritoneal dialysis fluid of the invention can be administered to patients which have not yet developed permeability disjunction.

In a preferred embodiment, the subject is at risk for renal failure, for example, the subject is a patient in end-stage renal failure.

In another aspect, the invention features, a peritoneal dialysis fluid which includes an inhibitor of a PKC.

In a preferred embodiment, the peritoneal dialysis fluid is one described herein.

In a preferred embodiment, an inhibitor of PKC is included in the peritoneal dialysis fluid. The inhibitor is preferably a specific inhibitor of PKC. The inhibitor can be an inhibitor of a PKC $\beta$, e.g., $\beta 1$ or $\beta 2$, $\gamma$, $\delta$, or other isoform, or combinations thereof. The inhibitor can be, for example, a bis (indolyl) maleimide, for example, the PKC $\beta$ inhibitor LY333531. LY333531 can be present in the dialysis fluid at about 1–1,000, 5–750, 20–500, but more preferably 50–500 nM.

In a preferred embodiment, the concentration of glucose in the peritoneal dialysis fluid is 200 nM.

In yet another aspect, the invention features, a method of making an improved peritoneal dialysis fluid. The method includes, providing a peritoneal dialysis fluid and adding to that fluid an inhibitor of a PKC, for example an inhibitor described herein, for example LY333531.

In a preferred embodiment, an inhibitor of PKC is included in the peritoneal dialysis fluid. The inhibitor is preferably a specific inhibitor of PKC. The inhibitor can be an inhibitor of a PKC β, e.g., β1 or β2, γ, δ, or other isoform, or combinations thereof. The inhibitor can be, for example, a bis (indolyl) maleimide, for example, the PKC β inhibitor LY333531. LY333531 can be present in the dialysis fluid at about 1–1,000, 5–750, 20–500, but more preferably 50–500 nM.

In a preferred embodiment, the concentration of glucose in the peritoneal dialysis fluid is 200 nM.

Subject, as used herein, can refer to a human subject, or a non-human animal, for example, a horse, cow, goat, pig, sheep or other veterinary, food or fiber producing animal, in need of dialysis. The subject can be an individual at risk for (e.g., the individual can have or be predisposed to have) end-stage renal disease, from any cause.

Other features and advantages of the invention will be apparent from the description herein and from the claims.

DETAILED DESCRIPTION OF THE DRAWINGS

DETAILED DESCRIPTION

Peritoneal dialysis for chronic renal failure is used by some patients with renal failure. The fluid for peritoneal dialysis uses glucose at 400-mM range. While not wishing to be bound by theory, it appears that at this concentration level, glucose causes complications which can lead to decreasing permeability between the peritoneal dialysis fluid and the blood compartment. The elevation of high glucose causes changes in the cells lining the peritoneum. The invention is based, in part on, PKC activation, which is believed to cause this chronic decrease in the exchange between the peritoneal fluid and a vascular compartment.

PKC activation induced by hyperglycemia either in the peritoneal fluid or in the blood causes cells to behave abnormally. The inhibition of PKC β isoform by the inhibitor LY333531 can prevent many of the vascular changes induced by glucose levels up to 20–30 mM. The higher concentration of glucose as used in peritoneal dialysis will also increase PCK activation. Inhibition of PKC activation using a PKC β, e.g., β1 or β2, γ, δ, or other isoform, or combinations thereof, inhibitor will prevent the thickening and the decrease in exchange between peritoneal and vascular compartments, which will improve the efficiency of peritoneal dialysis for chronic renal failure.

Figure 1:
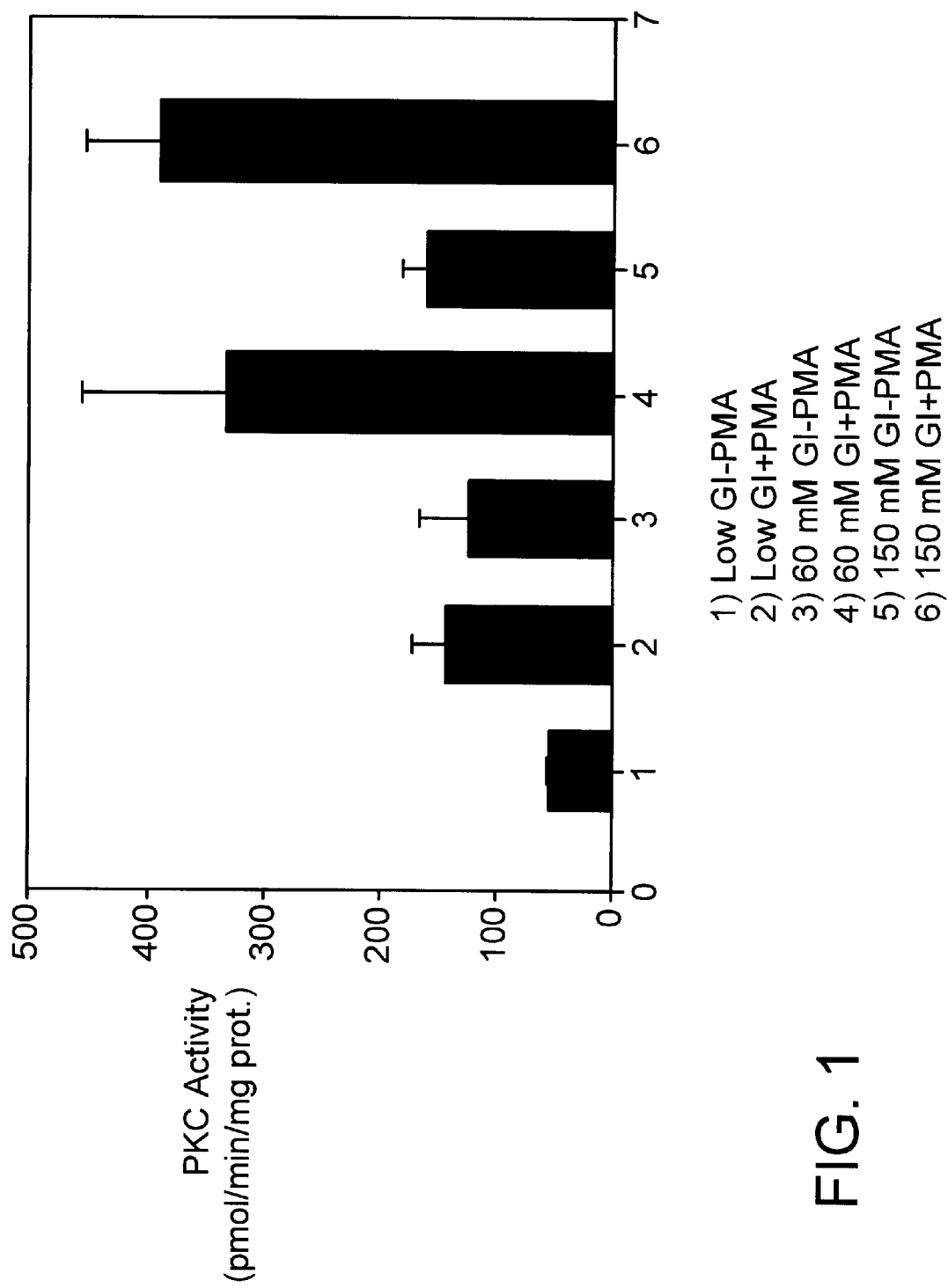
FIG. 1 shows PKC activity of primary human mesothelial cells at various glucose levels (i.e., low glucose, 60 mM or 150 mM glucose). The PKC activity was determined in the presence or absence or PMA, an activator of PKC.
Figure 2:
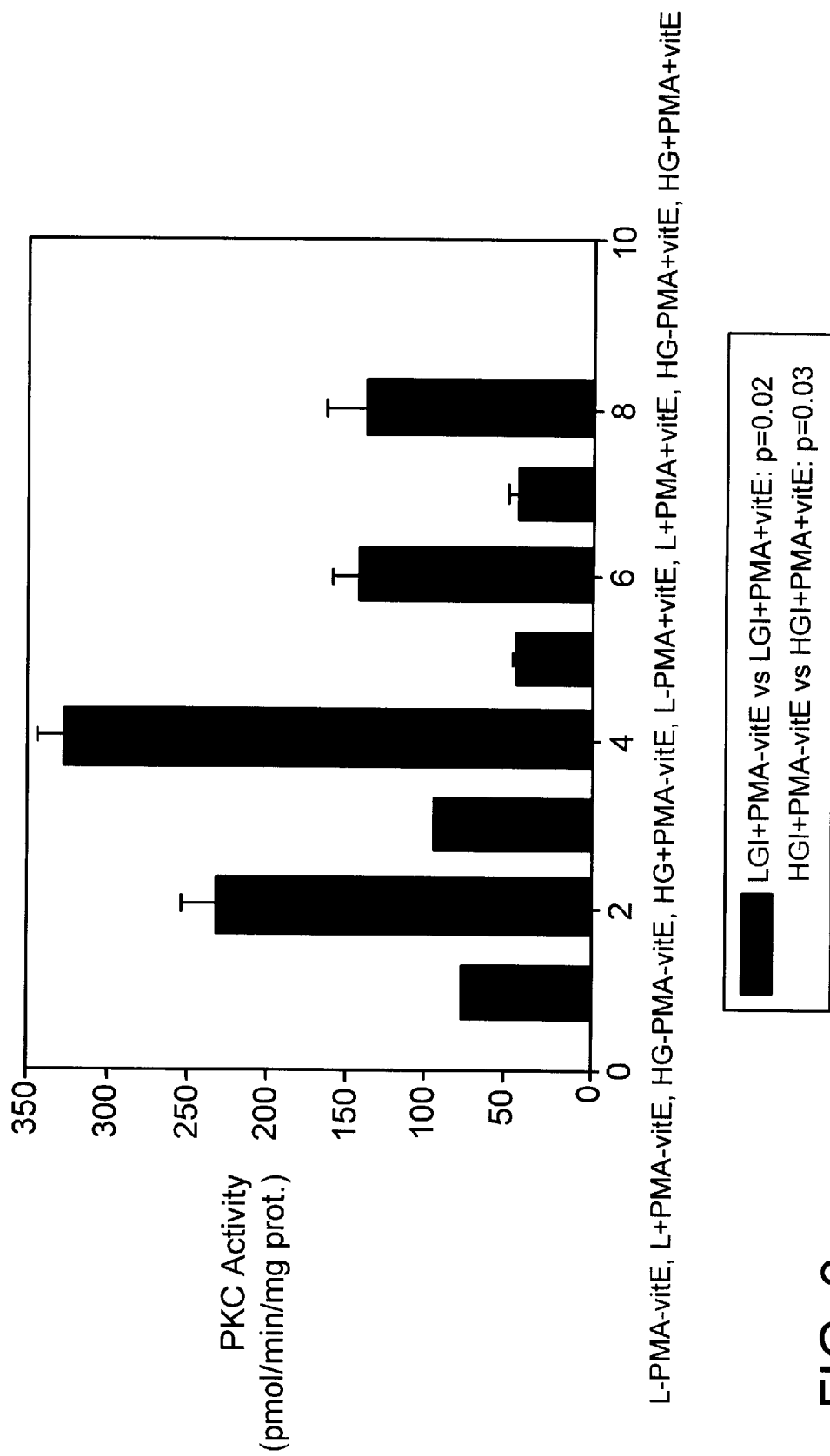
FIG. 2 shows the effect of treatment with vitamin E on PKC activity of human primary mesothelial cells. The mesothelial cells were exposed to low or high (150 mM) levels of glucose in the presence or absence of PMA, an activator of PKC, and the presence or absence of vitamin E, a PKC inhibitor.
Figure 3:
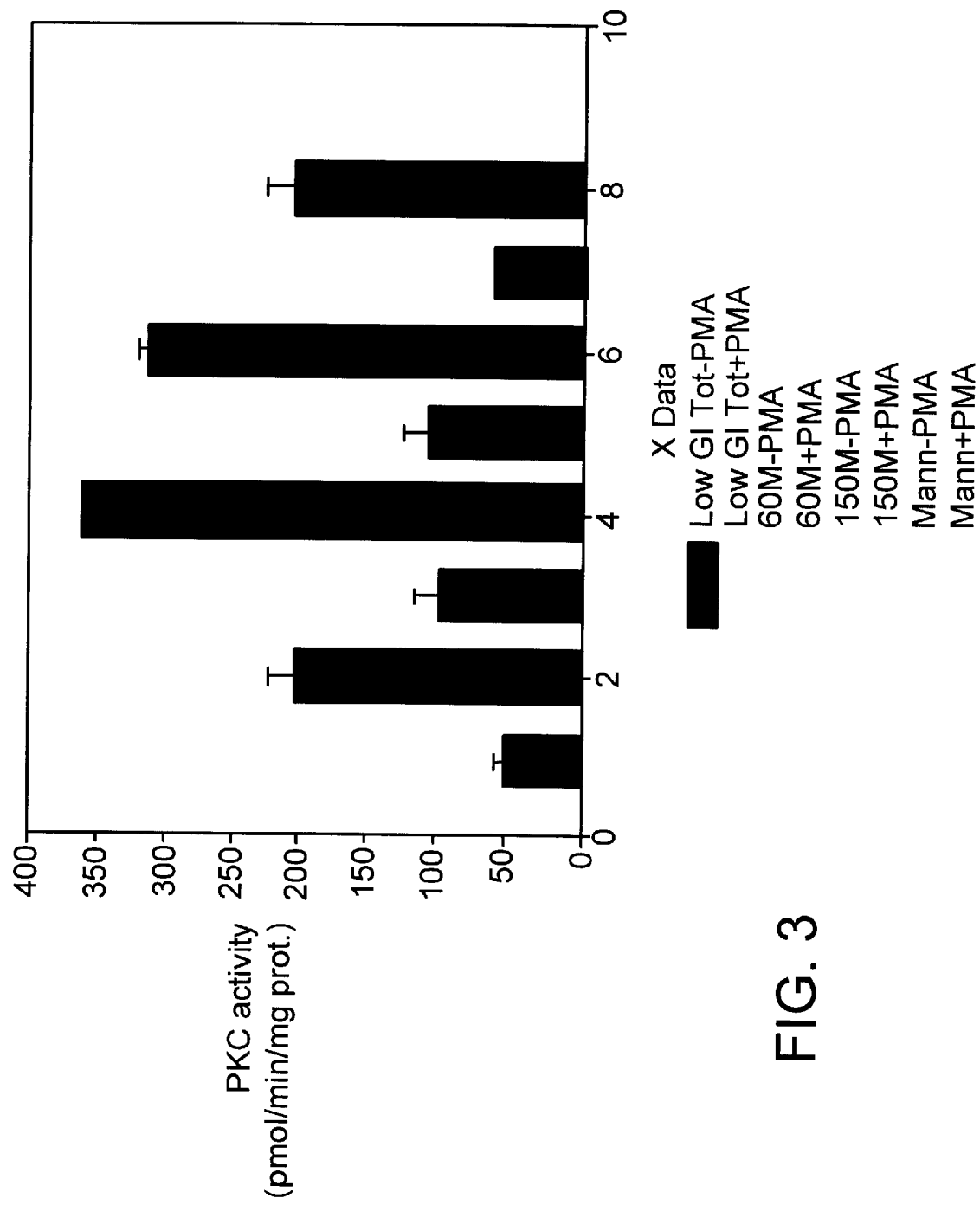
FIG. 3 shows PKC activity of primary human mesothelial cells cultured in low glucose concentrations, high glucose concentrations (i.e., 60 mM or 150 mM), or mannitol. The PKC activity was determined in the presence or absence or PMA, an activator of PKC.
Figure 4:
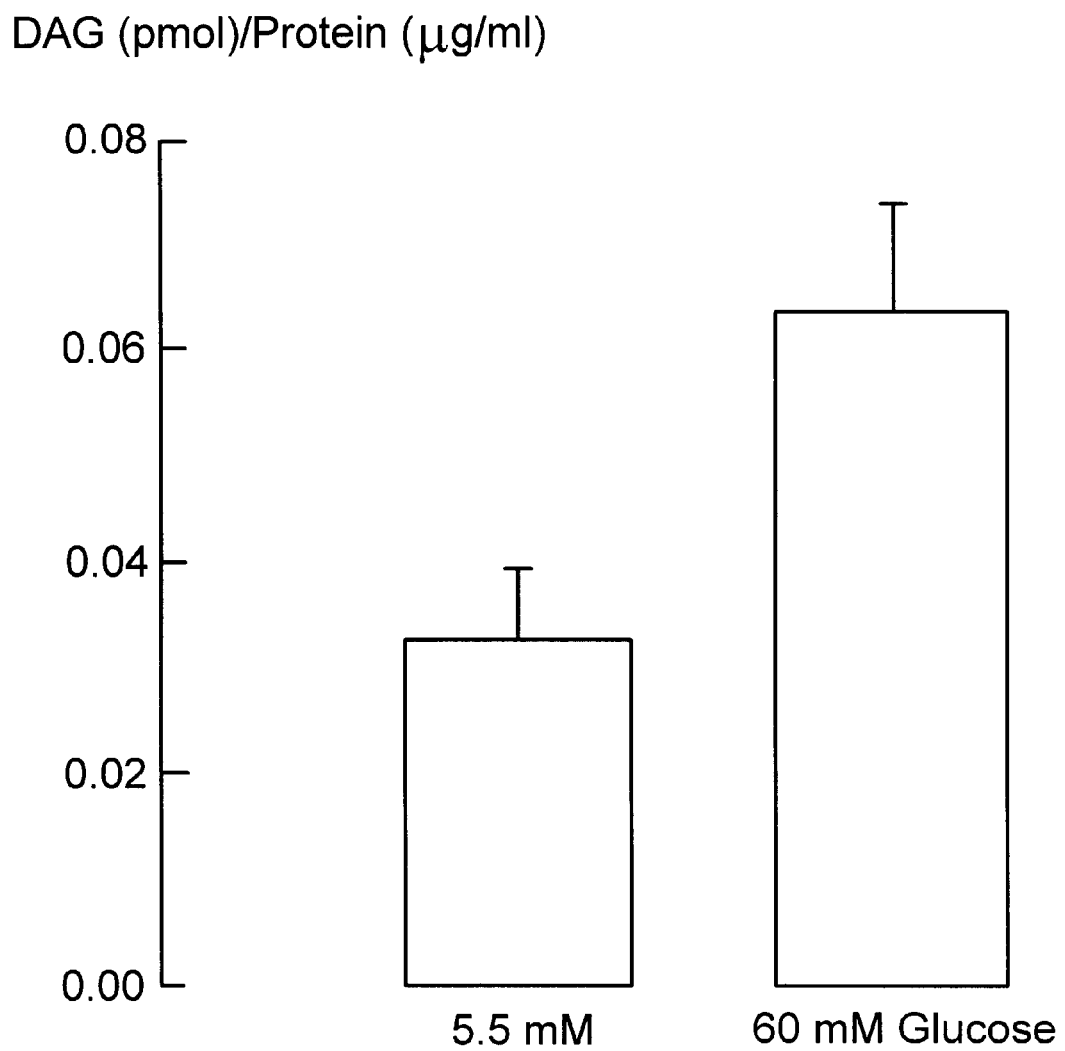
FIG. 4 shows DAG activity of transformed mesothelial cells at low glucose levels (5.5 mM) and high glucose levels (60 mM).

As shown in FIGS. 1–3, exposure of human mesothelial cells, which are the cells that line the peritoneum, to glucose levels of 60 mM or 150 mM results in an increase of PKC activity. These concentrations of glucose are standard for dialysis. In addition, as shown in FIG. 2, exposure of these cells to vitamin E, which is an inhibitor of PKC, resulted in a decrease of PKC activity. It was also found that high glucose levels of 60 mM or 150 mM increased DAG activity. These results demonstrate that glucose concentrations used for peritoneal dialysis activate the DAG-PKC pathways. It has been reported that activation of these pathways increases fibrosis. These results also show that inhibitors of PKC such as vitamin E decrease PKC activity. Therefore, inhibition of PKC can decrease fibrosis and reduce or prevent permeability failure of the peritoneal membrane.

Other embodiments are within the following claim.

What is claimed is:

1. A method of treating permeability failure in a subject, comprising:
    introducing into said subject a peritoneal dialysis fluid which includes a bis (indolyl) maleimide protein kinase C (PKC) inhibitor, thereby treating said subject.

2. The method of claim 1, wherein said inhibitor is LY333531.

3. The method of claim 2, wherein said LY333531 is present in said dialysis fluid at about 1–1,000 nM.

4. The method of claim 1, wherein said dialysis fluid has a concentration of glucose of about 200 nM.

5. The method of claim 1, wherein said subject has previously received peritoneal dialysis.

6. The method of claim 1, wherein said subject has been a peritoneal dialysis patient for at least 2 to 24 months.

7. The method of claim 1, wherein said subject has already developed permeability disjunction.

8. The method of claim 1, wherein said subject has not yet developed permeability disjunction.

9. The method of claim 1, wherein said subject is at risk for renal failure.

10. The method of claim 1, wherein said subject is in end-stage renal failure.

\* \* \* \* \*

UNITED STATES PATENT AND TRADEMARK OFFICE
CERTIFICATE OF CORRECTION

PATENT NO. : 6,753,341 B1
DATED : June 22, 2004
INVENTOR(S) : George Liang King

Page 1 of 1

It is certified that error appears in the above-identified patent and that said Letters Patent is hereby corrected as shown below:

Title page,
Item [73], Assignee, replace "Cancer" with -- Center --
Item [56], References Cited, OTHER PUBLICATIONS, "Sitter et al.," reference, (second occurrence) delete "Sitter et al., "High glucose increases prostaglandin E2 synthesisi in human peritoneal mesothelial cells: Role of hyperosmolarity.", Journal of the American Society of Nephrology, vol. 9, No.11, pp. 2005-2012, Nov. 1998."

Signed and Sealed this

Fifth Day of July, 2005

JON W. DUDAS
*Director of the United States Patent and Trademark Office*